United States Patent [19]
Steger et al.

[11] Patent Number: 5,855,571
[45] Date of Patent: *Jan. 5, 1999

[54] ABSORBENT ARTICLES CONTAINING SUPERABSORBENT MATERIAL WHICH HAS A DELAYED ACTIVATION TIME

[75] Inventors: Christina Steger, Torslanda; Edward Guidotti, Göteborg; Eje Österdahl, Västra Frölunda; Urban Widlund, Mölnlycke, all of Sweden

[73] Assignee: Molnlycke AB, Gothenburg, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 553,638
[22] PCT Filed: Jun. 13, 1994
[86] PCT No.: PCT/SE94/00572
  § 371 Date: Dec. 5, 1995
  § 102(e) Date: Dec. 5, 1995
[87] PCT Pub. No.: WO95/00183
  PCT Pub. Date: Jan. 5, 1995

[30] Foreign Application Priority Data

Jun. 21, 1993 [SE] Sweden .................................. 9302146

[51] Int. Cl.[6] ..................................................... A61F 13/15
[52] U.S. Cl. ........................................... 604/368; 604/378
[58] Field of Search ........................... 604/358, 367–368, 604/372, 385.1, 378

[56] References Cited

U.S. PATENT DOCUMENTS

| | | |
|---|---|---|
| 4,335,722 | 6/1982 | Jackson . |
| 4,341,215 | 7/1982 | Eldridge . |
| 4,548,847 | 10/1985 | Aberson et al. .......................... 604/368 |
| 4,699,823 | 10/1987 | Kellenberger et al. .................. 604/368 |
| 4,834,735 | 5/1989 | Alemany et al. ........................ 604/368 |

FOREIGN PATENT DOCUMENTS

WO 91/04361  4/1991  WIPO .

*Primary Examiner*—Robert A. Clarke
*Attorney, Agent, or Firm*—Burns, Doane, Swecker & Mathis LLP

[57] ABSTRACT

An absorbent structure in an absorbent article, such as a diaper, incontinence guard, sanitary napkin and the like, wherein the structure includes hydrophilic fibres and particles of a superabsorbent material and also has a front and a back part (4, 5) and a crotch part (6) located therebetween, said crotch part exhibiting a wetting region (16) within which the major part of discharged fluid is directed and wherein the absorbent structure in the wetting region includes superabsorbent particles that are encased in a material that will only dissolve slowly in and/or be penetrated slowly by the fluid to be absorbed so that the superabsorbent material will not begin to absorb fluid and swell to any appreciable extent until the encapsulating material has dissolved and/or been penetrated by the fluid and that conventional superabsorbent material (15) is localized generally in those parts of the structure that are located outside said wetting region.

15 Claims, 2 Drawing Sheets

ABSORBENT ARTICLES CONTAINING SUPERABSORBENT MATERIAL WHICH HAS A DELAYED ACTIVATION TIME

This application claims the benefit of international application PCT/SE94/00572 filed Jun. 13, 1994.

TECHNICAL FIELD

The present invention relates to an absorbent structure in an absorbent article, such as a diaper, incontinence guard, sanitary napkin and the like, which incorporates superabsorbent polymeric material in particle form, for instance in the form of grains, granules, flakes or fibres, which is highly effective in absorbing liquid, such as water and body fluids, for instance urine and blood, while swelling and forming a gel which will not dissolve in water.

BACKGROUND ART

So-called superabsorbents are polymers that are able to absorb fluid in quantities corresponding to many times their own weight. They are also able to retain the fluid absorbed even when subjected to external pressure. Such polymers have found wide use in absorbent sanitary products such as diapers, sanitary napkins and the like, said polymers normally being present in particle form, such as in the form of grains, granules, flakes or fibres, and are mixed or layered with other absorbent material, typically cellulose fibres.

The effectiveness of such superabsorbents in an absorbent structure is contingent on many factors, such as where and how the superabsorbent is incorporated in the absorbent structure, its particle form and physical and chemical properties, and also the speed at which it will absorb fluids, its gel strength and its ability to retain absorbed fluids. A phenomenon referred to as gel blocking may also influence negatively the absorbency of a fibre structure that contains superabsorbents. Gel blocking is a phenomenon in which when superabsorbent particles are wetted, they form a gel which blocks the pores in the fibre structure or the voids between the particles, therewith obstructing the transportation of fluid from the wetting area to the remainder of the absorbent body, and also obstructing the transportation of fluid to all particles. Another problem is that the superabsorbent particles located in the wetting region of the absorbent structure binds the fluid in said region already at the first wetting occasion. The acquisition at the next wetting occasions is by that deteriorated. In consequence, the total absorption capacity of the absorbent body is not utilized to an optimal extent and there is a risk that fluid will leak from the article. This problem is even more acute in the case of articles that are intended to be used over long periods of time, for instance throughout the night, where wetting often occurs on several occasions.

It is known through FR-A-2,627,080 to encapsulate superabsorbent particles in a protective membrane, which will only dissolve slowly in the fluid to be absorbed, e.g. urine. The activation of the superabsorbent material is by that delayed. The encapsulated superabsorbent particles can be applied in a layer closest to the body-facing side of the absorbent core.

It is known from EP-B-0,388,120 to mix superabsorbent particles with a porous silicon dioxide powder with the intention of reducing the hygroscopicity of the superabsorbents during storage and transportation. It is reported, however, that the absorption properties are not affected by this treatment.

WO 91/04361 teaches a method of encapsulating superabsorbent particles in a protective membrane. The protective membrane is comprised of a mixture that contains a film-forming polymer and a hydrophobic crystalline substance, and is intended to protect the particles against the absorption of fluid during the manufacture of an absorption structure by means of a wet-laying process. Subsequent to drying the structure, it is necessary to destroy the casing, for instance either mechanically or thermally, with the aid of ultrasound or the like, in order to make the superabsorbent particles active as fluid absorbents.

U.S. Pat. No. 4,548,847 describes a superabsorbent which has the form of an anionic polyelectrolyte which is reversibly cross-linked with a polyvalent metal cation. Also included is a substance which when coming into contact with fluid reacts with or binds to the metal cation to form a complex compound therewith. It is not until this has taken place that the superabsorbent is activated and able to start absorbing fluid. This results in a relatively short delay in the absorption process.

OBJECTS AND SUMMARY

An object of the present invention is to provide an absorbent article in which the transport of fluid from the wetting region of the absorbent structure to areas outside the wetting region can easily occur also at repeated wettings of the absorbent article.

This object has been achieved in accordance with the invention by that the superabsorbent material having delayed activation time is localized generally in the wetting region of said structure or in the close proximity of said wetting region, and that conventional superabsorbent material, i.e. material which is not encapsulated, is localized generally in those parts of the structure that are localized generally in those parts of the structure that are located outside said wetting region.

Individual superabsorbent particles may be contained in a casing of material which slowly dissolves in and/or is slowly penetrated by the fluid. Alternatively, several superabsorbent particles may be embedded in a common matrix of said material.

At most 30%, preferably at most 20%, and more preferably at most 10% of the total absorbency of the superabsorbent particles will preferably have been reached after five minutes, tested in accordance with the tea-bag method. Much longer delay times, for instance delay times in the order of one or more hours, before the particles will begin to absorb liquid to any greater extent after fluid contact are desirable in many applications.

The casing encapsulating the superabsorbent particles may be comprised of gelatine, microcrystalline cellulose, cellulose derivative, a surfactant substance, for instance.

The invention also relates to an absorbent article which incorporates superabsorbent particles of the aforesaid kind, optionally together with one or more different superabsorbent materials.

According to one embodiment, superabsorbent that has a delayed activation time is placed in a layer in the bottom of the structure, this layer being capable of functioning as a fluid-wicking layer. A separate fluid-wicking layer may also be placed beneath or above the structure. This dispersion layer contains superabsorbent that has a delayed activation time and may also function as a reserve capacity with repeated wetting of the article, but will not prevent wicking of the fluid.

The structure may include two or more superabsorbents which have different delayed activation times, either in a generally homogenous mixture or with different concentrations in different parts of the structure.

BRIEF DESCRIPTION OF THE DRAWINGS

The invention will now be described in more detail with reference to a number of exemplifying embodiments thereof and also with reference to the accompanying drawings, in which.

DESCRIPTION OF EXEMPLIFYING EMBODIMENTS

Figure 1:
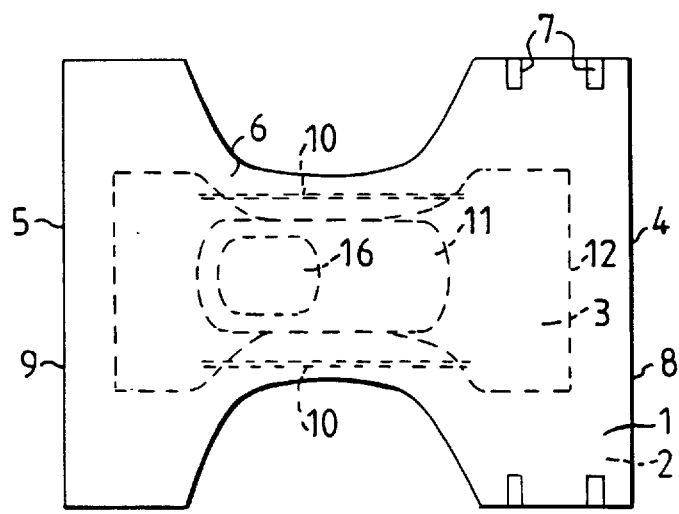
FIG. 1 is a top view of a diaper seen from the side that lies proximal to the wearer.

The diaper illustrated in FIG. 1 includes a fluid-permeable casing layer 1, made for instance of nonwoven fabric or perforated plastic film, a fluid-impermeable casing layer 2, for instance a plastic film or a hydrophobic nonwoven fabric, and an absorbent body 3 enclosed between the casing layers 1, 2.

The diaper is intended to embrace the lower part of the wearer's trunk like a pair of absorbent pants. To this end, the diaper includes a rear part 4 which is intended to lie rearwardly on the wearer, a front part 5 which is intended to lie forwardly on the wearer, and a narrower crotch part 6 which is located between the rear part and the front part of the diaper and which in use is intended to lie in the wearer's crotch between the wearer's legs. The diaper is secured in the desired pants-like configuration with the aid of fastener tabs 7 mounted in the region of the rear waist edge 8 of the diaper. The fastener tabs 7 are fastened onto the front part 5 of the diaper when the diaper is worn, close to the front waist edge 9, so as to hold the diaper around the wearer's waist.

The diaper illustrated in FIG. 1 also includes pre-stretched elastic devices 10, which may be comprised of elastic bands, covered elastic threads, elastic foam or some other appropriate material. For the sake of simplicity, the elastic devices 10 have been shown in a stretched state in FIG. 1. As soon as the tension in the elastic devices ceases, the devices will contract, however, to form elastic diaper leg openings.

In the case of the FIG. 1 embodiment, the absorbent body 3 of the diaper is comprised of two layers, i.e. an upper fluid-acquisition layer 11 and a lower fluid-storing and fluid-wicking layer 12. The upper, acquisition layer 11 shall be capable of quickly accommodating large quantities of fluid over a short period of time, i.e. have a high instantaneous fluid absorption capacity, whereas the lower storage and wicking layer 12 shall have a high fluid wicking capacity and be capable of draining fluid from the acquisition layer 11 and spreading the fluid throughout the storage and wicking layer 12. The differences in the properties of the two layers 11 and 12 can be achieved through differences in density, wherein a harder compressed fibre structure will disperse fluid more efficiently than a corresponding fibre structure of lower density, which due to its larger pore size will have a higher instantaneous fluid absorption capacity and lower wicking ability. Differences in the absorption properties of the two layers can also be achieved with the aid of different fibre structures which have different properties.

Thus chemically produced cellulose fluff pulp is able to disperse fluid to a greater extent than mechanical pulp or chemithermomechanical pulp, so-called CTMP, for instance. A fibre structure which includes chemically stiffened cellulose fibres also has a higher instantaneous fluid absorption capacity but lower fluid dispersiveness than conventional chemical pulp. The acquisition layer 11 may also conveniently be comprised of synthetic or natural fibre wadding or a fluffy nonwoven material.

Although the acquisition layer may be devoid of superabsorbent material, it will preferably include a given proportion of superabsorbent, between 2 and 30% and preferably between 2 and 15% of superabsorbent material, calculated on the total weight of the layer in its dry state, in the region or regions in which the superabsorbent is incorporated. The superabsorbent material is distributed generally uniformly in the layer, within at least one layer region, and is intended to absorb and to bind the fluid that remains in the layer 11 after fluid has been drained therefrom by the second wicking and storage layer 12. Because the acquisition layer 11 includes superabsorbents, a very dry surface is obtained, since the voids between the fibres are emptied of fluid. The superabsorbent 18 in the acquisition layer 11 will preferably have a high gel strength, i.e. will be able to swell and to retain fluid and remain essentially unaffected by those pressures that normally occur, so as not to block or prevent the dispersion of fluid. These superabsorbents are characterized by a high degree of cross-linking, which makes it more difficult to press the superabsorbents together than in the case of a gel which has a lower degree of cross-linking.

Figure 2:
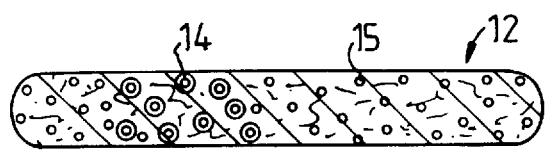
FIGS. 2–4 are schematic, longitudinal sectional views of an absorption layer according to various exemplifying embodiments of the invention.

The wicking and fluid-storage layer 12 also includes superabsorbent material. The proportion of superabsorbent in the layer 12 will preferably be between 2 and 90%, preferably between 10 and 80%, calculated on the total weight of the layer in a dry state. In the case of the embodiment illustrated in FIG. 2, the layer 12 includes two different types of superabsorbent 14 and 15, referenced with ⊙ and ○ respectively. The layer 12 of the exemplifying embodiment illustrated in FIG. 2 includes a first particulate absorbent 14 in and around the wetting area 16 of the diaper (FIG. 1), i.e. the area or region of the diaper with which body fluid discharged by the wearer first comes into contact with the diaper, this wetting region normally being displaced slightly towards the front part of the diaper, and the particles being encased in a material which will only be slowly dissolved by or be penetrated slowly by the fluid to be absorbed, for instance urine. The thus encapsulated superabsorbent will not swell and absorb fluid until the casing material has been dissolved and/or has been penetrated by the fluid. The acquisition layer 11 may also include encapsulated superabsorbent 14, which is able to function as a reserve capacity with repeated wetting of the diaper.

The term superabsorbent shall be given a relatively wide interpretation in the present context and may include both superabsorbent grains and superabsorbent granules, flakes and short fibres. The superabsorbents are comprised chemically of essentially water-insoluble cross-linked polymers and are found in a number of different chemical compositions. The chemical composition of the superabsorbent, however, has no significance to the present invention and it is thus possible to use any encapsulated particulate superabsorbent 14 whatsoever that has properties suitable for the purpose intended. Of course, mixtures of different superabsorbents may also be used. It can be said that the superabsorbent 14 shall exhibit a delayed activation time, i.e. swelling and fluid-absorption of the superabsorbent to an appreciable extent shall not commence at the first wetting of the diaper, but shall essentially retain its original particle size. This will not impair the dispersion of fluid from the wetting region to remaining parts of the wicking and storage layer 12, which contains a conventional superabsorbent 15 which begins to absorb fluid immediately upon fluid contact or only some few seconds after fluid contact. When fluid is subsequently discharged onto the diaper, the encapsulated superabsorbent 14 will be essentially unused and will therewith not prevent further dispersion or spreading of the fluid and can now begin to swell and absorb fluid, provided that its activation delay time has been exceeded.

The time taken to activate the encapsulated superabsorbent 14 will depend on the material chosen to encase the superabsorbent and also on the thickness of the casing, and can thus be adapted as desired. The activation time is conveniently adapted to the time lapse that can normally be expected before a second fluid discharge will occur, normally several hours. However, the activation time should correspond at least to the time taken for the fluid first delivered to the diaper to spread from the wetting region to those parts of the layer 12 which contain the conventional superabsorbent 15 and for this superabsorbent to be able to absorb the major part of the fluid. This time period will be at least five minutes, preferably at least fifteen minutes. More preferably, however, the activation time will be at least one hour. The activation time, however, can be adapted to the type of product concerned and also to the length of time that the product is intended to be in use.

The so-called tea-bag method is a suitable method of measuring the activation time. According to this method, 0.2 g of superabsorbent is placed in a bag which is made of polyester net, 5×5 cm, and the bag is then sealed around its perimeter. The bag is then placed in a bowl or basin containing a surplus of 0.9% NaCl-solution, wherein the sample is allowed to swell freely in the bag. The amount of sample used should not be so great as to cause the bag to limit absorption. The sample is removed from the salt solution at given times and the solution allowed to drain-off for one minute, whereafter the bag is weighed. The measuring process is considered to be complete when two mutually consecutive measurements indicate that solution is no longer being absorbed, wherewith it is assumed that the superabsorbent has absorbed solution to its total capacity.

The absorption capacity $A_1$ (g/g) of the superabsorbent is calculated by the formula:

$$A_1 = (W_1 - W_2)/0.2$$

where $W_1$ is the weight of the tea bag and sample after absorption, $W_2$ is the weight of the tea bag, and 0.2 is the dry weight of the sample.

In this case, the activation time is defined as the time taken for the superabsorbent to achieve a given percentage of its total absorption capacity. Thus, according to the invention, the superabsorbent shall have reached at most 30%, preferably at most 20% and more preferably at most 10% of its total absorption capacity in some cases after five minutes, in other cases after fifteen minutes or sometimes even after one hour or more.

The material used to encapsulate the superabsorbent may, for instance, be similar to the material used to encapsulate drugs for delayed release, and may, for instance, be a gelatine capsule, a casing comprised of microcrystalline cellulose, cellulose derivative, a surfactant coating or some other material which is slowly degraded or slowly through-wetted by the fluid to be absorbed. The casing may either be comprised of a material which will dissolve slowly in the fluid to be absorbed or which is insoluble in said fluid but has a porosity which enables the fluid to penetrate slowly through the material. When the encapsulated superabsorbent particles come into contact with the fluid, they begin to swell and the outer casing will eventually crack.

The border between the different superabsorbents 14 and 15 in the layer 12 may either be relatively distinct or continuous, so that the superabsorbents will be mixed with one another in a transition zone.

Figure 3:
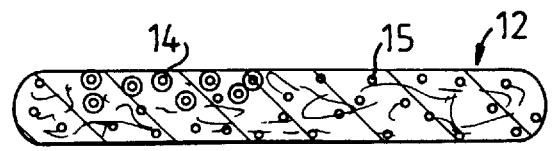

In the case of the embodiment illustrated in FIG. 3, the encapsulated superabsorbent 14 is incorporated in and around the wetting region 16, although only in the upper part of the layer 12, whereas the conventional superabsorbent 15 is incorporated in the regions outside the wetting point and in the lower part of the layer 12, even opposite the wetting region.

Figure 4:
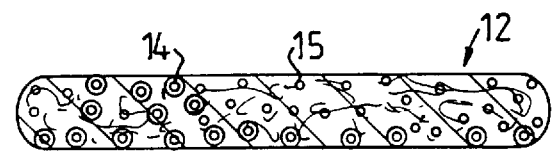

FIG. 4 illustrates a further exemplifying embodiment in which the encapsulated superabsorbent 14 is included in the wetting region and also in the bottom of the layer 12. This arrangement will not prevent fluid spreading along the bottom of the layer 12, and fluid is able to spread to essentially the same extent as in a pure pulp layer. Activation of the superabsorbent 14 enables the hitherto essentially unused absorption capacity of the article to be utilized to the full. It is also conceivable to arrange a separate wicking layer beneath or on top of the storage layer. This wicking layer may include encapsulated superabsorbent 14, which provides a reserve capacity in those cases when fluid is repeatedly discharged by the wearer.

Several different encapsulated superabsorbents 14 having mutually different activation times may be used, wherein the superabsorbent which has the longest activation time is placed in the wetting region, while another superabsorbent having a shorter activation time is placed outwardly of, and so on. The superabsorbent which has the shortest absorption time is placed distal from the wetting point. In this case, the activation times can be adapted to the expected times of subsequent wetting occasions, i.e. the second, third wetting occasion and so on. As will be understood, the borders between the different types of superabsorbents need not be distinct, but may be continuous so that a mixture of the various superabsorbents will be found in certain parts of the absorption layer. It is also possible to use a mixture of superabsorbents that have different activation times in the whole or parts of the absorbent core.

Figure 5:
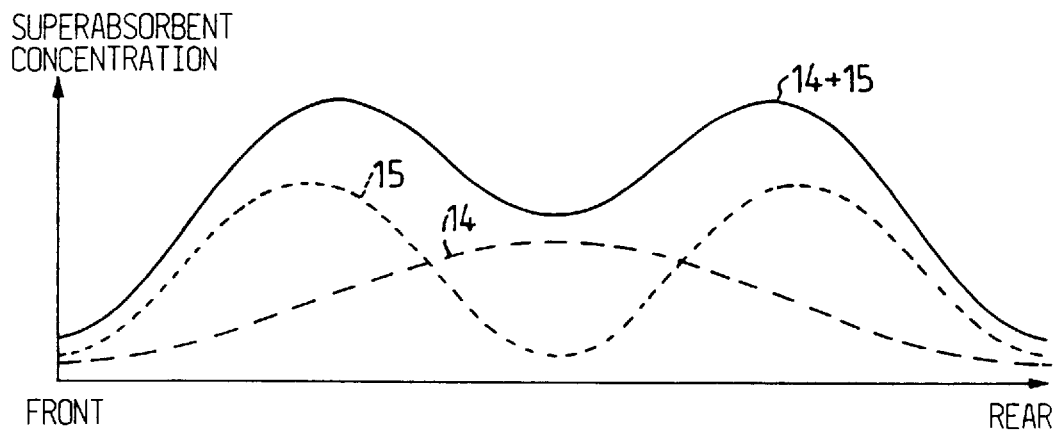
FIGS. 5 and 6 are diagrams which illustrate the variation in superabsorbent concentration in the longitudinal direction of a diaper, in accordance with a couple of exemplifying embodiments.

FIG. 5 illustrates another variant in which the total superabsorbent concentration, shown with a full line, has a gradient in the longitudinal direction of the absorption layer 12. In the illustrated case, the encapsulated superabsorbent 14, the concentration gradient of which is shown with broken lines, has a highest concentration in the wetting region with decreasing concentration in a direction towards the front and the rear end-parts of the absorption layer 12. The conventional superabsorbent 15 exhibits a bilobal concentration gradient, shown in chain lines, in the longitudinal direction of the layer, so that the highest concentration will lie in the regions located just outside the wetting region, with decreasing concentration out towards the end-parts and in towards the wetting region.

The combined superabsorbent concentration, shown with a full line, is highest in those regions that lie just outside the wetting region, and is lower in the actual wetting region and decreases outwards towards the end-parts. This provides effective use of the superabsorbents.

Figure 6:
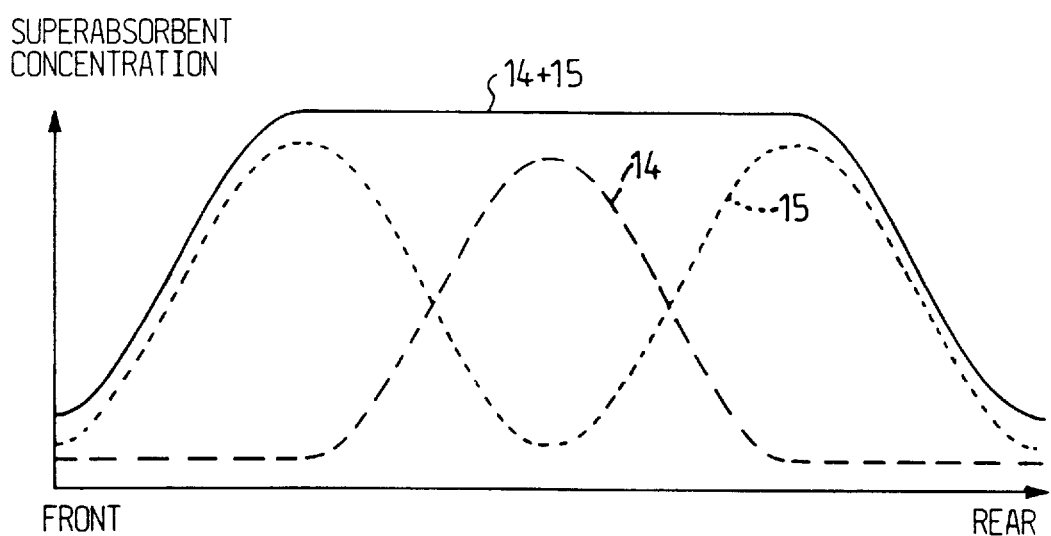

In the case of the FIG. 6 embodiment, the concentration of encapsulated superabsorbent has been increased so as to obtain a uniform total distribution of superabsorbent in the centre part of the absorption layer.

The two figures show the wetting region to be located in the centre of the absorption layer. It will be understood, however, that the wetting region may be displaced, for instance, towards the front part of the absorption layer, with a corresponding displacement of the concentration gradients. In some cases two or more wetting regions may be provided, since the location of the wetting region depends on the position of the user, lying down, standing up etc.

Optionally, all of the embodiments described above may include a small amount of conventional superabsorbent 15 admixed in those parts of the absorption layer which contains the encapsulated superabsorbent 14, for instance the wetting region, so as to absorb any remaining fluid in the fibre network that has not drained to other parts of the absorbent body. It is also conceivable to place conventional superabsorbent 15 in a thin zone uppermost in the absorption layer 12, so as to enhance the surface dryness of the absorbent article.

The invention is primarily intended for diapers which are intended to be worn over a long period of time, for instance throughout the night, when fluid is often discharged on several occasions. It will be understood, however, that the invention is not limited to the illustrated exemplifying embodiments thereof and that modifications can be made within the scope of the following claims. For instance, the superabsorbents 14 and 15 may be applied in layers instead of being mixed with the fibres in the structure. Neither need the conventional superabsorbent 15 have a particle form, but may be in sheet form, for instance.

In other respects, the configuration and construction of the diaper is quite optional and the invention can be applied to all types of diaper, incontinence guard, sanitary napkin, etc. The absorbent body may also be configured in many different ways, for instance in the form of a single layer or in several layers. In addition to cellulose fibres, the fibre structure in which the superabsorbent is incorporated in accordance with the invention may comprise other, optional hydrophilic fibres, either natural or synthetic fibres, which have absorption properties suitable for the purpose intended. The superabsorbent may also be applied between layers of tissue, for instance.

We claim:

1. An absorbent structure in an absorbent article, such as a diaper, incontinence guard, or sanitary napkin, the structure comprises:

hydrophilic fibers;

particles of a superabsorbent material; and a front and a back part and a crotch part located therebetween;

said crotch part having a wetting region to which a major part of discharged fluid is directed;

some of the superabsorbent particles are encased in a material that will only dissolve slowly in the discharged fluid to be absorbed, so that the some superabsorbent particles have a delayed activation time and will not begin to absorb the discharged fluid and swell to any greater extent until the encapsulating material is dissolved, wherein the some superabsorbent particles having delayed activation time are localized generally in the wetting region of said structure, and that a remainder of the superabsorbent particles, i.e., which are not encapsulated, are localized primarily in parts of the structure that are located outside said wetting region.

2. The absorbent structure according to claim 1, wherein the parts of the structure which include the superabsorbent particles having delayed activation time also include a given proportion of the remainder of superabsorbent particles.

3. The absorbent structure according to claim 1, wherein the superabsorbent particles having a delayed activation time are localized in a bottom zone of the structure.

4. An absorbant structure according to claim 1, wherein the structure includes a fluid-wicking layer which contains the some superabsorbent particles having a delayed activation time.

5. The absorbent structure according to claim 1, wherein two or more of the some superabsorbent particles having a delayed activation time have different activation times and are included in the structure, either in an essentially homogenous mixture or with different concentrations in different parts of the structure.

6. The absorbent structure according to claim 5, wherein a first of the two or more superabsorbent particles which has a longest activation time is localized primarily in and in close proximity of the wetting region of the structure or an upper zone of the structure nearest the wearer, whereas a second of the two or more superabsorbent particles having a shorter activation time is localized primarily in those parts of the structure that are located outside those parts which contain the first superabsorbent particles; and in that the remainder of the superabsorbent particles are localized primarily distal from the wetting region.

7. The superabsorbent material according to claim 1, wherein the encapsulating material is one of gelatine, microcrystalline cellulose, cellulose derivative and a surfactant coating.

8. An absorbent structure in an absorbent article, such as a diaper, incontinence guard, or sanitary napkin, the structure comprises:

hydrophilic fibers;

particles of a superabsorbent material; and a front and a back part and a crotch part located therebetween, said crotch part having a wetting region to which a major part of discharged fluid is directed;

wherein at least some of the superabsorbent particles are encased in a material that will only be penetrated slowly by the discharged fluid to be absorbed, so that the at least some superabsorbent particles have a delayed activation time and will not begin to absorb the discharged fluid and swell to any greater extent until the encapsulating material has been penetrated by the fluid, wherein the at least some superabsorbent particles having delayed activation time are localized generally in the wetting region of said structure, and that a remainder of the superabsorbent particles, i.e., which are not encapsulated, are localized primarily in parts of the structure that are located outside said wetting region.

9. The absorbent structure according to claim 8, wherein the parts of the structure which include the superabsorbent particles having delayed activation time also include a given proportion of the remainder of superabsorbent particles.

10. The absorbent structure according to claim 8, wherein the superabsorbent particles having a delayed activation time are localized in a bottom zone of the structure.

11. The absorbent structure according to claim 8, wherein the structure includes a fluid-wicking layer which contains the some superabsorbent particles having a delayed activation time.

12. The absorbent structure according to claim 8, wherein two or more of the some superabsorbent particles having a delayed activation time have different activation times and are included in the structure, either in an essentially homogenous mixture or with different concentrations in different parts of the structure.

13. The absorbent structure according to claim 12, wherein a first of the two or more superabsorbent particles which has a longest activation time is localized primarily in and in close proximity of the wetting region of the structure or an upper zone of the structure nearest the wearer, whereas a second of the two or more superabsorbent particles having a shorter activation time is localized primarily in those parts of the structure that are located outside those parts which contain the first superabsorbent particles; and in that the remainder of the superabsorbent particles are localized primarily distal from the wetting region.

14. The absorbent structure according to claim 8, wherein the encapsulating material is one of gelatine, microcrystalline cellulose, cellulose derivative and a surfactant coating.

15. The absorbent structure according to claim 8, wherein said structure includes a first layer and a second layer, said at least some encapsulated superabsorbent particles being disposed within said wetting region in an upper part of said second layer and at least some of said superabsorbent particles being disposed within said wetting region in a lower part of said second layer.

* * * * *